Oct. 17, 1967 W. S. LEE Plant Pat. 2,773
JUNIPER PLANT
Filed July 1, 1966
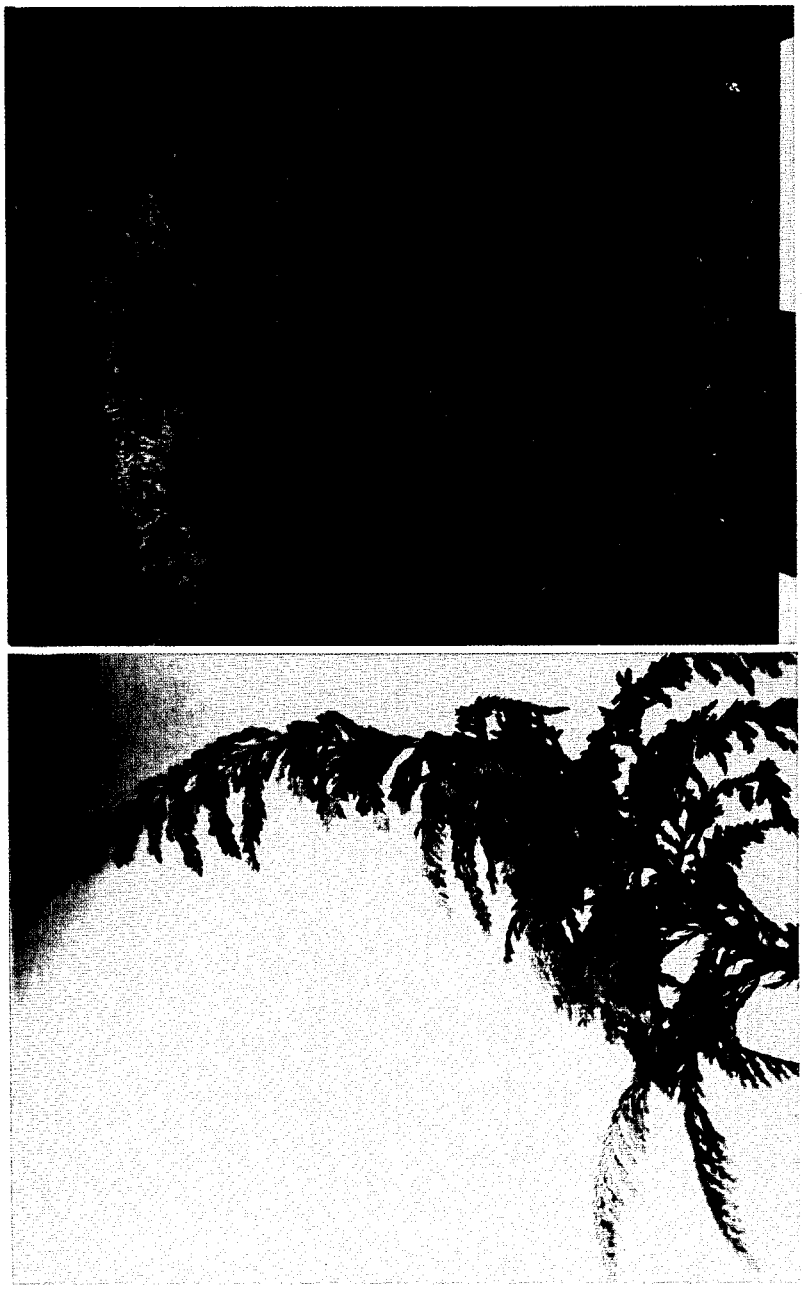
INVENTOR.
WALTER S. LEE,
By Edmond F. Shanahan
ATTORNEY.

United States Patent Office

Plant Pat. 2,773
Patented Oct. 17, 1967

2,773
JUNIPER PLANT

Walter S. Lee, Bellflower, Calif., assignor to Monrovia Nursery Co., Azusa, Calif., a corporation of California Filed July 1, 1966, Ser. No. 563,637
1 Claim. (Cl. Plt.—50)

The present invention relates to a new and distinct variety of the genus Juniperus.

The plant is characterized as to novelty by its low and spreading habit of growth and by its distinctive blue-green coloring. The specific known variety most like the new variety is *Juniperus horizontalis petraeus,* an unpatented variety; however the present variety has distinct differences.

I discovered the original plant accidentally as a seedling, originating in 1953. The plant has been reproduced asexually by cutting and grafts. This plant does not reproduce from seed; seedlings revert to the variety found in *Juniperus horizontalis* generally The new variety is shown in full color in the accompanying composite illustration. A detailed description follows:

*The plant*

Parentage: Chance seedling resulting from open pollination.

*Pollen parent.*—Unknown.

*Seed parent.*—*Juniperus horizontalis.*

Growth: The plant is remarked for its low and spreading habit of growth. Branches are long and procumbent. Oldest plants are now 7 years old, and at present, are approximately less than 6 inches in height, with a spread of over three feet.

Branches: The new growth of the branches is blue-green in color, gradually shading to a light tan and then to a reddish-brown with maturity.

Growth habit: The new variety differs from the plant it most closely resembles (*Juniperus horizontalis petraeus*) in several ways: the center of the plant fills in with foliage, and this center does not brown or burn out when subjected to summer temperatures of up to 110 degrees. No artificial handling or pruning has been practiced on the plant to make it grow low and procumbent.

Foliage: The foliage is soft and feathery. New growth has sparse foliage, but as the branches mature, it fills in to form a dense mat. No imbricated scale-like foliage has been noted on any of the plants to the present time.

Shape and arrangement: Leaves are oppositely arranged, densely crowded on branchlets; subdulate (awl-like) on both new and mature growth. The upper side of the leaf shows two glaucus bands confluent near the apex of the leaf and two glaucus spots at the base of the underside of the leaf. The underside of the leaf is remotely keeled.

Color: Blue-green.

Flower: No flower or cones have been noted, and it is not known whether the plants are pistillate or staminate.

I claim:

A new and distinct variety of juniper plant, substantially as herein described and illustrated, and characterized particularly as to novelty by its low and spreading habit of growth and by its distinctive blue-green coloring.

No references cited.

ABRAHAM G. STONE, *Primary Examiner.*

ROBERT E. BAGWILL, *Examiner.*